(12) United States Patent
Sankaran et al.

(10) Patent No.: US 9,239,905 B1
(45) Date of Patent: *Jan. 19, 2016

(54) SYSTEMS AND METHODS FOR TREATMENT PLANNING BASED ON PLAQUE PROGRESSION AND REGRESSION CURVES

(71) Applicant: HeartFlow, Inc., Redwood City, CA (US)

(72) Inventors: Sethuraman Sankaran, Palo Alto, CA (US); Charles A. Taylor, San Mateo, CA (US); Gilwoo Choi, Mountain View, CA (US); Michiel Schaap, Mountain View, CA (US); Christopher K. Zarins, Menlo Park, CA (US); Leo J. Grady, Millbrae, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/621,129

(22) Filed: Feb. 12, 2015

Related U.S. Application Data

(63) Continuation of application No. 14/522,343, filed on Oct. 23, 2014.

(60) Provisional application No. 62/033,446, filed on Aug. 5, 2014.

(51) Int. Cl.
*G06F 19/26* (2011.01)
*G06F 19/00* (2011.01)

(52) U.S. Cl.
CPC .......... *G06F 19/3437* (2013.01); *G06F 19/325* (2013.01); *G06F 19/3431* (2013.01)

(58) Field of Classification Search
None
See application file for complete search history.

(56) References Cited

U.S. PATENT DOCUMENTS

| 8,315,812 | B2 | 11/2012 | Taylor et al. |
| 2012/0041323 | A1 | 2/2012 | Taylor et al. |
| 2013/0132054 | A1 | 5/2013 | Sharma et al. |

FOREIGN PATENT DOCUMENTS

WO    WO 2013/019840 A1    2/2013

OTHER PUBLICATIONS

Winnifred van Lankeren, et al.; Plaque area increase and vascular remodeling contribute to lumen area change after percutaneous transluminal angioplasty of the femoropopliteal artery: An intravascular ultrasound study, Journal of Vascular Surgery, vol. 29, No. 3, pp. 430-441, 1999 LAC annotated.
U.S. Appl. No. 14/011,151, filed Aug. 27, 2013 entitled "Systems and Methods for Predicting Location, Onset, and/or Change of Coronary Lesions".
U.S. Appl. No. 13/864,996, filed Apr. 17, 2013 entitled "Method and System for Sensitivity Analysis in Modeling Blood Flow Characteristics".
U.S. Appl. No. 14/254,481, filed Apr. 16, 2014, entitled "Systems and Methods for Predicting Coronary Plaque Vulnerability from Patient-Specific Anatomic Image Data".
U.S. Appl. No. 14/447,195, filed Jul. 30, 2014, entitled "Method and System for Modeling Blood Flow with Boundary Conditions for Optimized Diagnostic Performance.".
U.S. Appl. No. 13/895,893, filed May 16, 2013, entitled "Systems and Methods for Estimating Blood Flow Characteristics from Vessel Geometry and Physiology".
U.S. Appl. No. 13/895,871, filed May 16, 2013, entitled "Systems and Methods for Estimating Ischemia and Blood Flow Characteristics from Vessel Geometry and Physiology".
Parodi O et al.; "Patient-Specific Prediction of Coronary Plaque Growth From CTA Angiography: A Multiscale Model for Plaque Formation and Progression", IEEE Transactions on Information Technology in Biomedicine, IEEE Service Center, Los Alamitos, CA, US, vol. 16, No. 5, Sep. 1, 2012, pp. 952-965.
Jingliang Dong et al.: "Image-based computational hemodynamics evaluation of atherosclerotic carotid bifurcation models", Computers in Biology and Medicine, vol. 43, No. 10, Oct. 1, 2013, pp. 1353-1362.
International Search Report and Written Opinion for corresponding PCT Application No. PCT/US2015/043565, dated Oct. 14, 2015, (12 pages).
Koskinas et al. (American Journal of Cardiology (2012) vol. 110:318).
Nozou et al. (American Journal of Cardiology (2012) vol. 109: 1247-1253).

*Primary Examiner* — Lori A Clow
(74) *Attorney, Agent, or Firm* — Bookoff McAndrews, PLLC

(57) ABSTRACT

Systems and methods are disclosed for evaluating a patient with vascular disease. One method includes receiving patient-specific data regarding a geometry of the patient's vasculature; creating an anatomic model representing at least a portion of a location of disease in the patient's vasculature based on the received patient-specific data; identifying one or more changes in geometry of the anatomic model based on a modeled progression or regression of disease at the location; calculating one or more values of a blood flow characteristic within the patient's vasculature using a computational model based on the identified one or more changes in geometry of the anatomic model; and generating an electronic graphical display of a relationship between the one or more values of the calculated blood flow characteristic and the identified one or more changes in geometry of the anatomic model.

20 Claims, 10 Drawing Sheets

SYSTEMS AND METHODS FOR TREATMENT PLANNING BASED ON PLAQUE PROGRESSION AND REGRESSION CURVES

RELATED APPLICATION(S)

This application is a continuation of nonprovisional U.S. patent application Ser. No. 14/522,343, filed Oct. 23, 2014, which claims priority to U.S. Provisional Application No. 62/033,446, filed Aug. 5, 2014, the entire disclosures each of which are hereby incorporated herein by reference.

FIELD OF THE DISCLOSURE

Various embodiments of the present disclosure relate generally to disease assessment, treatment planning, and related methods. More specifically, particular embodiments of the present disclosure relate to systems and methods for treatment planning based on coronary plaque progression/regression curves.

BACKGROUND

Coronary artery disease is a common ailment that affects millions of people. Coronary artery disease may cause the blood vessels providing blood to the heart to develop lesions, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack. Significant strides have been made in the treatment of coronary artery disease including both medical therapy (e.g. statins) or surgical alternatives (e.g., percutaneous coronary intervention (PCI) and coronary artery bypass graft surgery (CABG)). For example, PCI and CABG may be implemented where lesions are detected. However, some artery blockage may not be functionally significant. In other words, a blockage may not require surgical intervention if the blockage does not significantly obstruct flow and interfere with oxygen delivery to heart muscle.

One important hemodynamic measure used in the diagnosis of functionally significant lesions is fractional flow reserve ("FFR"). FFR may quantify the ratio of pressure at a distal location in the coronary artery to the aortic pressure. This ratio is seen as indicative of the likelihood that a stenosis is functionally significant. Risky, expensive, and invasive catheterization of the coronary artery is traditionally used to measure FFR. However, recent advances may show that FFR may be calculated non-invasively using blood flow modeling and coronary computed tomography scans. In other words, FFR measurements or predictions may be more readily available with the recent developments in non-invasive acquisition of FFR.

However, the genesis and progression of coronary disease involves a complex combination of chemical, biological, and mechanical pathways across molecular, cellular, and tissue scales that is yet to be fully understood. Thus, a desire still exists to provide more accurate data relating to coronary lesions, e.g., size, shape, location, functional significance (e.g., whether the lesion impacts blood flow), etc. For example, understanding the geometry of vascular disease may involve studying the growth and remodeling of plaque (e.g., in coronary vascular disease).

In some cases, plaque characteristics may influence growth and remodeling of plaques. For example, calcified plaques may be typically stable and may not significantly remodel. Further, calcified plaques may be less receptive to medical therapy, for instance, statin treatment. In contrast, fatty and fibro-fatty plaques with a lipid core may have a higher remodeling index, and may be more receptive to medical therapy and lifestyle changes (e.g. exercise). In addition to plaque characteristics, factors including hemodynamic forces, plaque composition, plaque location, intramural stress, etc. may also contribute to the ability of plaque to remodel.

Thus, a desire exists to better understand the mechanism of how plaque geometry impacts the functional significance of disease (e.g., FFR) in a patient's vasculature. By extension, a desire exists to improve an understanding of pathogenesis and disease progression or regression. An improved understanding of the relationship between plaque geometry and pathogenesis may advance treatment planning, decreasing the frequency of unnecessary invasive treatment and ensuring selection of treatment effective for specific patient and disease plaque characteristics.

The foregoing general description and the following detailed description are exemplary and explanatory only and are not restrictive of the disclosure.

SUMMARY

According to certain aspects of the present disclosure, systems and methods are disclosed for treatment planning based on plaque progression and regression curves. For example, such systems and methods may include identifying which coronary artery plaques are sensitive to progression, stability or regression and the consequent effect on blood flow and pressure in the effected artery.

One method includes: receiving patient-specific data regarding a geometry of the patient's vasculature; creating an anatomic model representing at least a portion of a location of disease in the patient's vasculature based on the received patient-specific data; identifying one or more changes in geometry of the anatomic model based on a modeled progression or regression of disease at the location; calculating one or more values of a blood flow characteristic within the patient's vasculature using a computational model based on the identified one or more changes in geometry of the anatomic model; and generating an electronic graphical display of a relationship between the one or more values of the calculated blood flow characteristic and the identified one or more changes in geometry of the anatomic model.

In accordance with another embodiment, a system for evaluating a patient with vascular disease comprises: a data storage device storing instructions for evaluating a patient with vascular disease; and a processor configured for: receiving patient-specific data regarding a geometry of the patient's vasculature; creating an anatomic model representing at least a portion of a location of disease in the patient's vasculature based on the received patient-specific data; identifying one or more changes in geometry of the anatomic model based on a modeled progression or regression of disease at the location; calculating one or more values of a blood flow characteristic within the patient's vasculature using a computational model based on the identified one or more changes in geometry of the anatomic model; and generating an electronic graphical display of a relationship between the one or more values of the calculated blood flow characteristic and the identified one or more changes in geometry of the anatomic model.

In accordance with another embodiment, a non-transitory computer readable medium for use on a computer system containing computer-executable programming instructions for performing a method of evaluating a patient with vascular disease, the method comprising: receiving patient-specific data regarding a geometry of the patient's vasculature; creating an anatomic model representing at least a portion of a location of disease in the patient's vasculature based on the received patient-specific data; identifying one or more changes in geometry of the anatomic model based on a modeled progression or regression of disease at the location; calculating one or more values of a blood flow characteristic within the patient's vasculature using a computational model based on the identified one or more changes in geometry of the anatomic model; and generating an electronic graphical display of a relationship between the one or more values of the calculated blood flow characteristic and the identified one or more changes in geometry of the anatomic model.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

As described above, the functional significance of changes in arterial plaque geometry may be assessed using fractional flow reserve (FFR). FFR is recognized as an important hemodynamic measure for diagnosing the functional significance of lesions. FFR may quantify the ratio of pressure at a distal location in the coronary artery to the aortic pressure. The impact of plaque geometry on FFR (and thereby, blood flow) in a patient-specific coronary vasculature has not been well understood or quantified. Therefore, a desire exists to improve understanding of how atherosclerotic disease progression or regression alters plaque geometry and impacts blood flow.

Thus, the present disclosure is directed to techniques for automatically evaluating and electronically displaying the relationship between changes in plaque geometry and the functional significance of a lesion associated with the plaque geometry. In other words, the present disclosure is directed to systems and methods for determining how the growth/shrinkage of plaque geometry affects hemodynamics. In one embodiment, the present disclosure describes a system and method to understand the impact of lumen geometry on hemodynamic disease indicators. Predictive modeling of functional significance in response to changes in plaque geometry may help treatment planning for an individual. Specifically, the understanding of the impact may be combined with plaque characteristics to arrive at an optimal treatment strategy (e.g., as described in further detail in FIG. 2).

In one embodiment, the impact of lumen geometry on disease progression for an individual may be measured based on predictive modeling of plaque growth/shrinkage. Plaque progression/regression and tissue remodeling may be predicted by either (i) using computational modeling of the adaptive response of arterial walls in response to altered pressure or flow (from homeostatic conditions) or biological factors (e.g., hypertension, cholesterol level, activity level, smoking, etc.) or (ii) employing machine learning to predict plaque progression and vulnerability using features (e.g., plaque location, presence of proximal/distal disease, hypertension, cholesterol, activity level, smoking, etc.). Exemplary methods for machine learning approaches are disclosed, for example, in U.S. Nonprovisional application Ser. No. 14/011, 151, filed Aug. 27, 2013, entitled "Systems and Methods for Predicting Location, Onset, and/or Change of Coronary Lesions," which is hereby incorporated by reference herein in its entirety. In some cases, FFR values calculated using these machine learning techniques may be referred to as $FFR_{ML}$.

Figure 6:
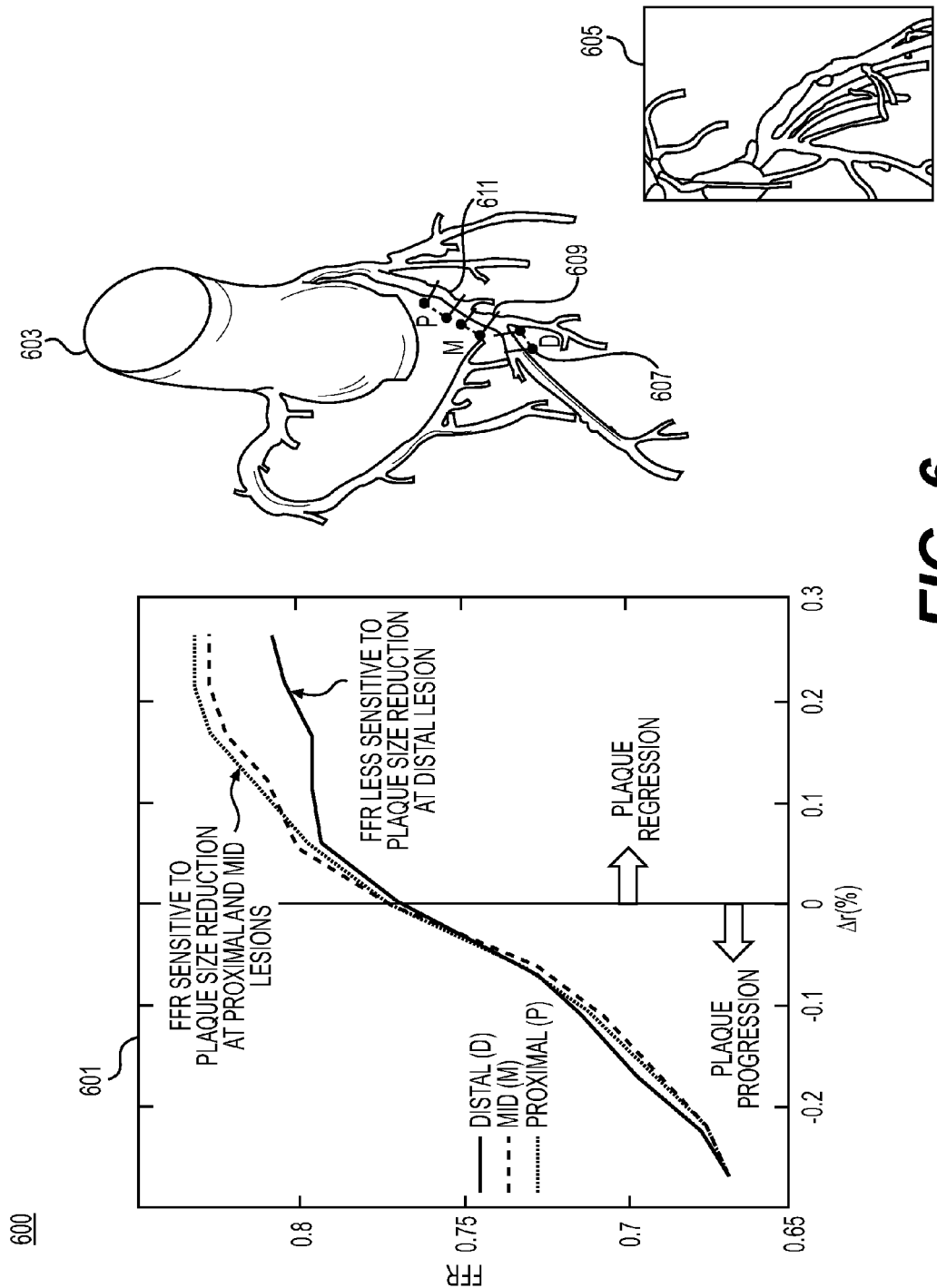
FIG. 6 shows an exemplary display including plaque progression/regression curves for a soft lipid-rich plaque, according to an embodiment of the present disclosure.
Figure 7:
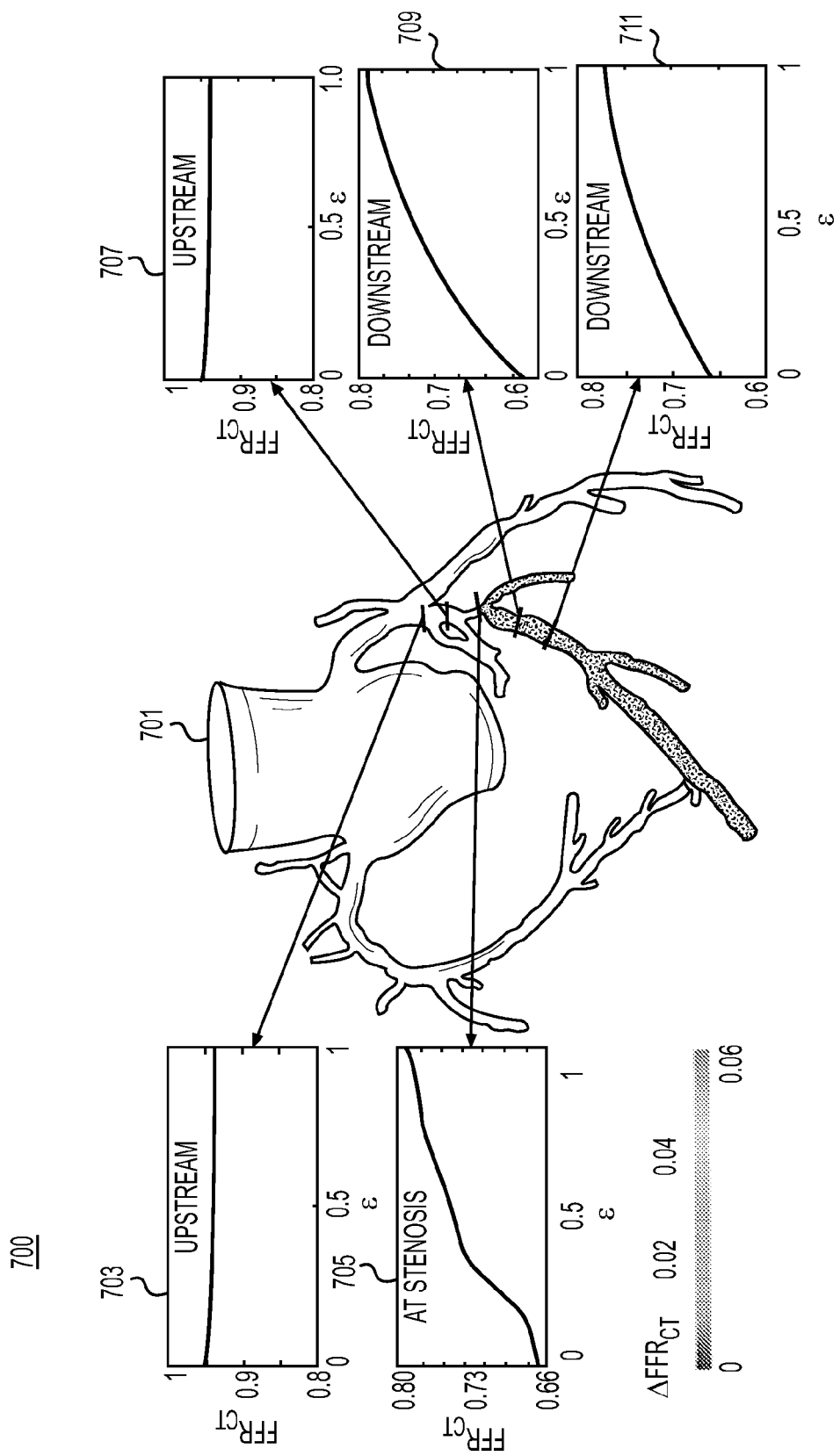
FIG. 7 shows an exemplary display of $FFR_{CT}$ variation due to remodeling of a lesion, according to an embodiment of the present disclosure.

A combination of plaque remodeling index, along with variability in FFR assessed using a statistical method, may be used to calculate the risk of plaque progression. In one embodiment, the variability of FFR, in response to the plaque remodeling index, may be recognized as hemodynamic sensitivity. Sensitivity analysis may also be used to characterize how FFR responds to changes in radius or minimum lumen diameter (MLD), for example, in the form of $FFR_{CT}$ vs. MLD curves (as shown in FIGS. 6 and 7). In one embodiment, the sensitivity curve may be calculated by performing one or both of: three-dimensional (3-D) simulations or machine learning analysis on candidate geometries identified by a stochastic collocation algorithm. Alternatively, a Monte-Carlo algorithm or a similar sampling of uniformly spaced geometries may be used to calculate the sensitivity curve. The slope of the $FFR_{CT}$ vs. MLD curve may be used to calculate the effect of plaque progression (e.g., where the slope is negative) and regression (e.g., where the slope is positive).

If plaque progression has low risk or $FFR_{CT}$ has low sensitivity to geometry, $FFR_{CT}$ sensitivity due to plaque progression may be low. A machine learning approach may be trained to predict sensitivity with respect to plaque progression by combining the features to predict plaque remodeling above, along with features to predict $FFR_{ML}$ (e.g., lumen area, hemodynamic factors (such as net downstream resistances), etc.). An exemplary method for estimating $FFR_{CT}$ sensitivity is disclosed, for example, in U.S. Nonprovisional application Ser. No. 13/864,996, filed Apr. 17, 2013, entitled "Method and System for Sensitivity Analysis in Modeling Blood Flow Characteristics," which is hereby incorporated herein by reference herein in its entirety.

In one embodiment, outputs may be quantified and visualized by coloring lesions based on the impact of a lesion on $FFR_{CT}$. The outputs may include one or a combination of (a) patient-specific geometry, where each lesion may be color-coded by its impact on $FFR_{CT}$, (b) a new $FFR_{CT}$ map in remodeled geometry, one for each lesion, (c) a characteristic progression/regression curve for each lesion, and/or (d) a quantified and output risk score based on a combination of remodeling index and $FFR_{CT}$ sensitivity to plaque geometry. Such visual outputs may be used to stratify highly sensitive lesions and assess the impact of medical therapy (e.g., for plaques that are sensitive to regression) or more frequent follow-ups (e.g., for patients who have lesions that have a negative functional significance (e.g., negative $FFR_{CT}$ diagnosis) but are sensitive to progression). A desire thus exists to determine such information, as it may be useful in predictive simulations of how remodeling of plaque morphology impacts $FFR_{CT}$.

The present disclosure also describes systems and methods for predicting how progression and regression of lesions affect $FFR_{CT}$, using a classification system. For example, a taxonomy chart may be created for treatment options (e.g., statin therapy, stenting, etc.) or lifestyle changes based on the type of lesion, baseline $FFR_{CT}$, and a calculated progression/regression curve. Placement on the taxonomy chart may be based on (a) the propensity of a lesion to remodel (e.g., soft plaques) and (b) the extent to which $FFR_{CT}$ is impacted when the lesion remodels. The present disclosure may provide: (i) a prediction of how progression/regression of disease (e.g., lesions) effects $FFR_{CT}$ based on disease type, (ii) a selection of treatment options based on progression/regression of lesions, and/or (iii) a quantified and output risk score based on a combination of remodeling index and $FFR_{CT}$ sensitivity to plaque geometry.

One embodiment for determining such information may include a broad taxonomy using a combination of (i) lesion type (e.g., calcified/fibrotic or lipid rich) and (ii) classification of lesions as hemodynamically sensitive or hemodynamically insensitive. Lipid-rich lesions that may be hemodynamically sensitive may be candidates for either medical therapy or PCI. Calcified lesions, independent of hemodynamic sensitivity, may be stable, whereas lipid-rich lesions that may be hemodynamically insensitive may be indeterminate. As will be described in more detail below, FIG. 2 includes an exemplary taxonomy for treatment planning based on the impact of plaque characteristics and remodeling on hemodynamics.

Overall, predictive modeling of plaque growth/shrinkage, as well as the interaction between plaque geometry and functional significance of the lesion may help in treatment planning of the patient, including making decisions on, for example, (i) whether aggressive medical therapy is optimal for the patient, (ii) time intervals at which a follow-up imaging study may preferentially be performed for the patient, and/or (iii) whether stenting and/or bypass grafting are suitable treatment options for a patient. The present disclosure is directed at quantifying the relation between plaque geometry and functional significance by plotting $FFR_{CT}$ at candidate measurement locations against plaque radius for each identified plaque (+/−25% MLD). Such plots may help assess the cost and benefits for surgical treatment options, medical therapy, and/or continuous monitoring.

Figure 1:
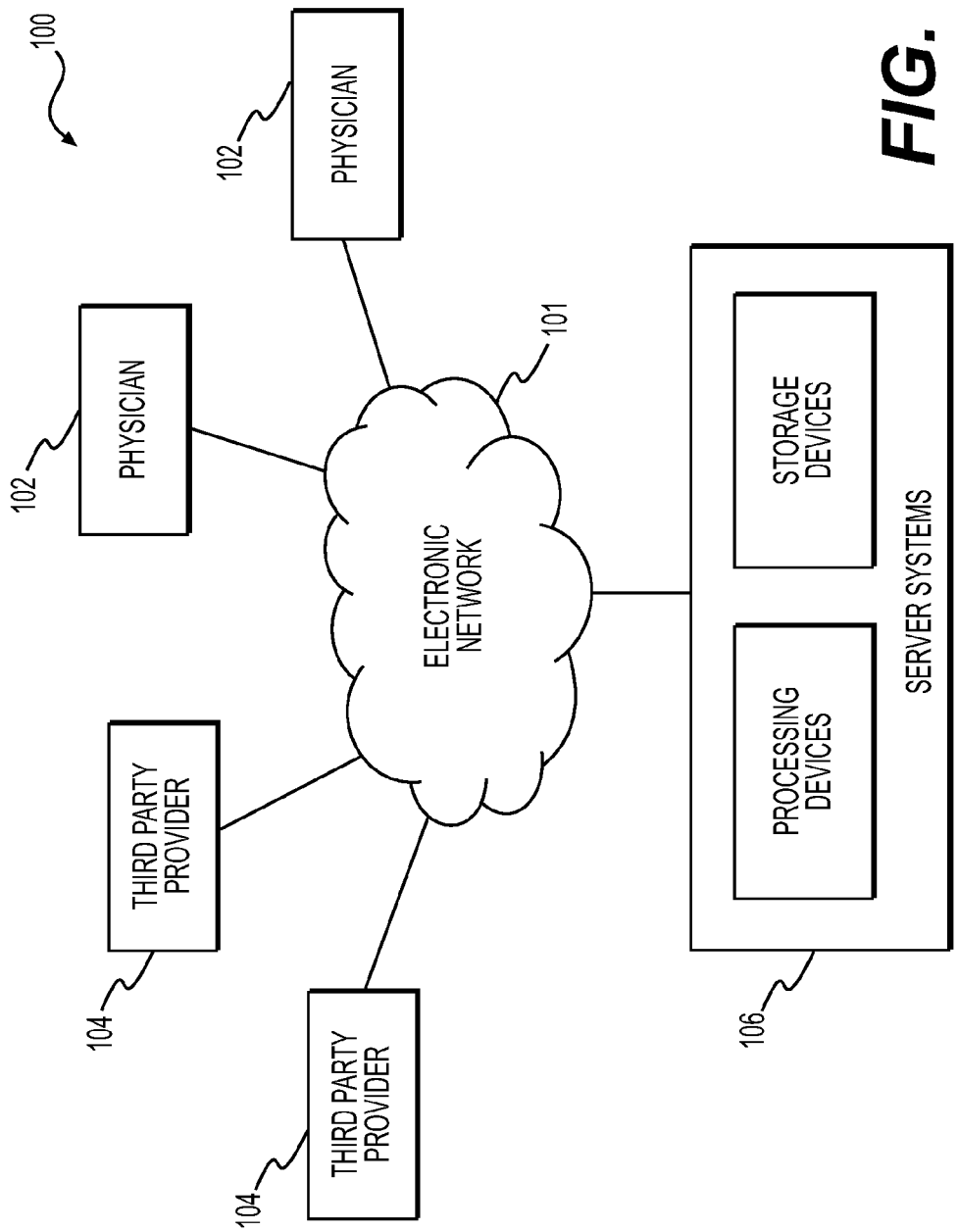
FIG. 1 is a block diagram of an exemplary system and network for treatment planning based on plaque progression and regression curves, according to an exemplary embodiment of the present disclosure.

Referring now to the figures, FIG. 1 depicts a block diagram of an exemplary system 100 and network for treatment planning based on plaque progression/regression curves, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific information, such as age, medical history, blood pressure, blood viscosity, etc. Physicians 102 and/or third party providers 104 may transmit the anatomical images and/or patient-specific information to server systems 106 over the electronic network 101. Server systems 106 may include storage devices for storing images and data received from physicians 102 and/or third party providers 104. Server systems 106 may also include processing devices for processing images and data stored in the storage devices.

Figure 2:
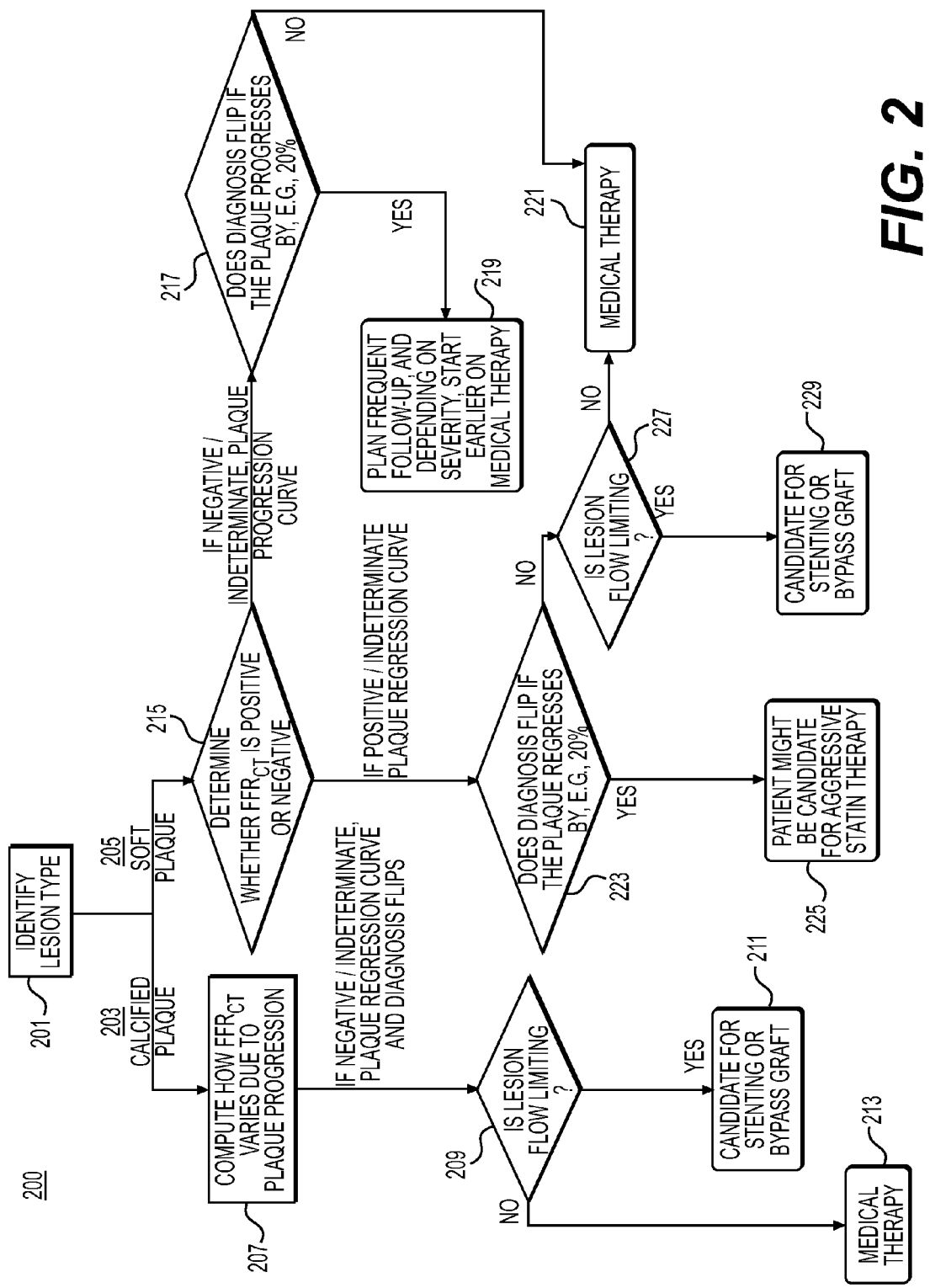
FIG. 2 is a block diagram of an exemplary method of treatment planning based on lesion type and hemodynamic sensitivity, according to an exemplary embodiment of the present disclosure.

FIG. 2 is a block diagram of an exemplary schematic of a method 200 of treatment planning based on lesion type and hemodynamic sensitivity, according to an exemplary embodiment. In one embodiment, method 200 includes a sequence and/or a taxonomy for classifying plaques detected in an individual's vasculature. In classifying the plaques, method 200 may guide treatment planning toward treatments suitable for the plaque characteristics associated with the classification.

In one embodiment, method 200 may include step 201 of identifying a lesion type (e.g., for a lesion detected in a patient's anatomy from CT or other digital imaging received at server systems 106). In one embodiment, method 200 may distinguish between lesion types broadly, as either calcified/fibrotic plaque 203 or soft plaque 205. Calcified or fibrotic plaques may be predominantly stable, so assessments may focus on whether the calcified or fibrotic plaques are candidates for stenting. Such assessments may include evaluating the extent to which the calcified or fibrotic plaques limit flow, and making a determination regarding stenting based on the level of flow blockage caused by the plaque.

If a patient lesion is identified as being comprised of calcified or fibrotic plaque 203, method 200 may proceed to step 207 may include computing variation of $FFR_{CT}$ in relation to plaque progression. As discussed above, FFR describes the ratio of pressures distal to a lesion and proximal to a lesion (e.g., $FFR=P_{distal}/P_{proximal}$). In one embodiment, $P_{proximal}$ may be measured in the aorta. Large pressure drops may be indicative of significant stenosis, meaning, functionally significant lesions may be associated with low FFR values. High FFR values (e.g., values closer to FFR=1) may indicate non-significant stenosis. For example, some embodiments may include an FFR threshold value of 0.8, where FFR>0.8 may indicate a negative diagnosis, or insignificant stenosis. By contrast, if FFR≤0.8, an associated lesion may receive a positive diagnosis, meaning significant stenosis.

Step 207 of computing $FFR_{CT}$ may be used in subsequent step 209, which may include determining if a lesion of calcified or fibrotic plaque is flow limiting. In one embodiment, a lesion may be identified as flow limiting if it is classified as having an FFR value of less than or equal to a predetermined threshold, e.g., FFR 0.8, and non-flow-limiting if it is classified as having an FFR value greater than a predetermined threshold, e.g., FFR>0.8. If the lesion is, in fact, flow limiting, the lesion may receive a "positive" diagnosis, meaning that significant stenosis exists at the lesion site. In such a situation, method 200 may proceed to step 211, which may include identifying the patient lesion as a candidate for stenting and/or bypass grafting. Since calcified plaques are less likely to regress, treatments recommended at step 211 may tend to include stenting or bypass grafts, rather than, for example, statin therapy. Alternately, step 209 may return an assessment that the patient lesion is not flow-limiting. In such a case, method 200 may proceed to step 213, which may involve recommending standard medical therapy to reduce risk factors for disease and/or recommending merely following-up periodically.

Where a patient lesion is identified as being a lipid-rich lesion of soft plaque 205, step 201 may be followed by step 215. Step 215 may include computing how $FFR_{CT}$ varies due to plaque progression or regression by first determining whether an $FFR_{CT}$ value calculated in relation to the plaque is negative or positive (i.e., respectively, above or below a predetermined threshold). Since soft plaque may be more hemodynamically sensitive than calcified or fibrotic plaque, step 215 may include an observation of $FFR_{CT}$ response to plaque regression. By contrast, step 207 may focus on only plaque progression, since calcified plaque may have a lower likelihood of regression.

Where step 215 determines that a lesion is not significant (i.e., $FFR_{CT}$ is negative), step 215 may be followed by step 217, which may include determining whether the lesion becomes significant if plaque progresses by, for example, 20%. For instance, step 217 may make this determination from a plaque progression curve of $FFR_{CT}$ against plaque geometry. If the lesion becomes significant from plaque progression past a given point (step 217, "Yes"), then step 219 may include recommending that the lesion be monitored. For example, treatment may not yet be necessary, but step 219 may include recommending frequent follow-ups and starting medical therapy if the lesion becomes more severe. If the lesion does not become significant, even with plaque progression (step 217, "No"), then step 221 may include determining that standard medical therapy is warranted to reduce risk factors for atherosclerosis.

Where step 215 involves determining that the lesion is, in fact, significant (i.e., $FFR_{CT}$ is diagnosed as positive, then step 215 may be followed by step 223, which may include determining whether the lesion becomes no longer functionally significant, should the plaque regress a given amount (e.g., 20% regression). If plaque regression changes the functional significance of the lesion (step 223, "Yes"), then step 223 may be followed by step 225, which may include recommending a treatment including aggressive medical therapy. For example, step 225 may identify a patient as a candidate for aggressive statin therapy and/or lifestyle changes (e.g., exercise). If plaque regression is modeled as not changing a functional significance of the lesion (step 223, "No"), then step 223 may be followed by step 227, which may include determining whether the lesion is flow-limiting. If the lesion is not identified as flow-limiting, then step 227 may be followed by step 221, including determining that treatment or action may be recommended for the lesion. If the lesion is flow-limiting, however, step 227 may be followed by step 229, where the lesion may be identified as a candidate for stenting and/or bypass grafting.

Figures 3A, 3B:
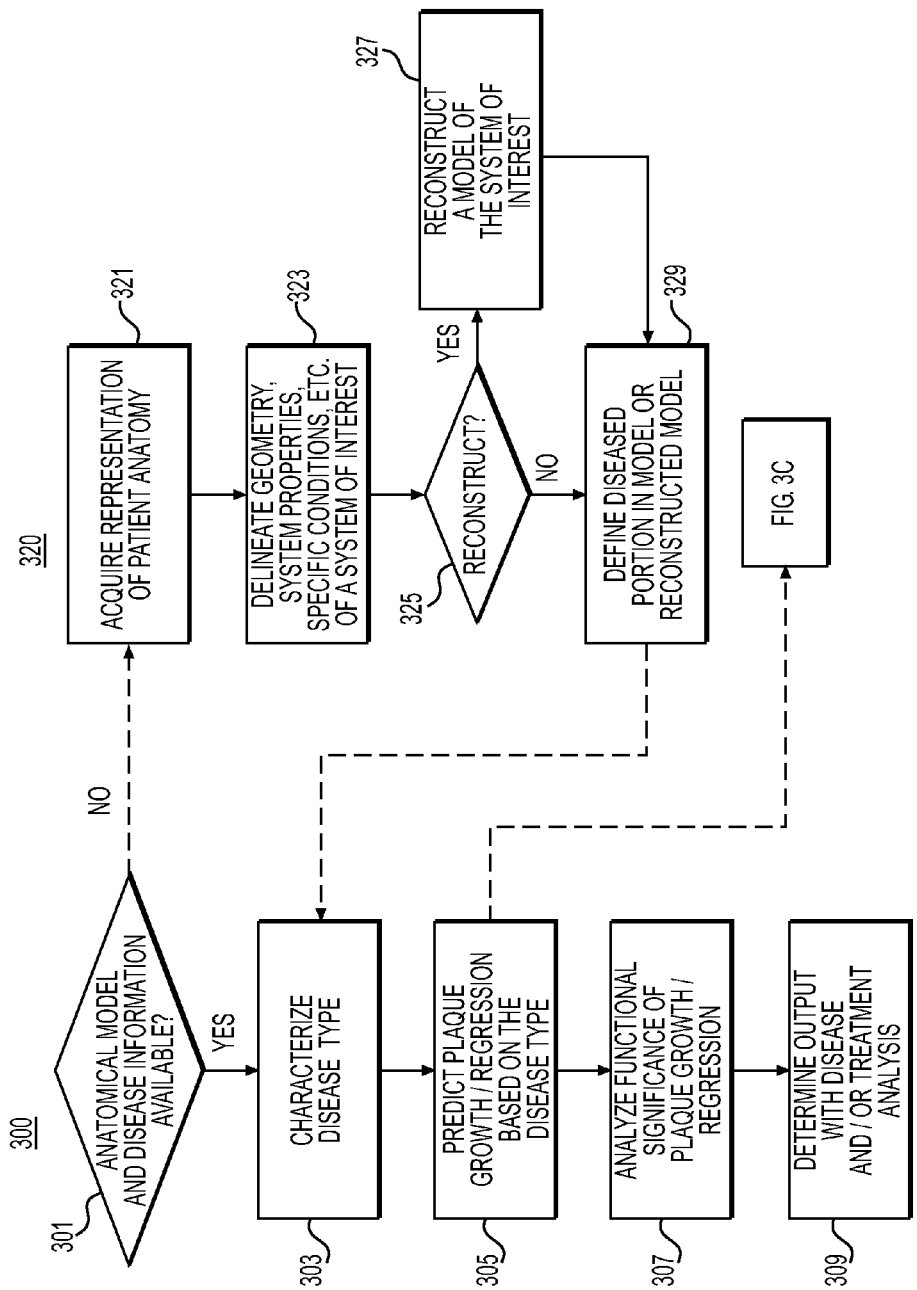
FIG. 3A is a block diagram of an exemplary method of treatment planning based on progression/regression curves, given specific patient characteristics, according to an exemplary embodiment of the present disclosure.
FIG. 3B is a block diagram of an exemplary method of creating an anatomical model including diseased regions, according to an exemplary embodiment of the present disclosure.

FIG. 3A is a block diagram of an exemplary method 300 of treatment planning based on progression/regression curves in light of specific patient characteristics, according to an exemplary embodiment. The method of FIG. 3A may be performed by server systems 106, based on information, images, and data received from physicians 102 and/or third party providers 104 over electronic network 101.

In one embodiment, step 301 may include determining whether an anatomical model and/or disease information is available. Where an anatomical model and information regarding disease type or location(s) of disease for the anatomical model is not available, steps may be taken to acquire such information. FIG. 3B describes an embodiment for model and/or information acquisition.

In one embodiment, step 303 may include characterizing a disease type from the anatomical model. In some embodiments, the characterization may include parameters (e.g., anatomical parameters, including changes in vessel radius), such that portion(s) of a patient anatomical model that match the characterization may be identified as diseased. For example, step 303 may include characterizing disease type based on a CT scan (e.g., accessed from step 301) and locations identified as diseased (e.g., available from step 301 or from method 320 of FIG. 3B). In some instances, step 303 may include characterizing disease type based on anatomy, composition of plaque, or a combination thereof. Determining disease type may further involve accounting for a number of factors, including location of disease, thickness of wall, material properties of the wall, metabolic activity of constituents in the wall, etc. In some embodiments, disease type may be characterized using a quantitative metric comprising combinations of the factors above. In one embodiment, step 303 may include creating the disease characterization. In other embodiments, step 303 may include receiving a characterization of a disease.

In one embodiment, step 305 may include predicting plaque growth/regression. In other words, whereas step 303 may include detecting disease, and more specifically, a present state of disease based on the patient anatomical model (e.g., from step 301), step 305 may involve forming an understanding of future states of the disease. Treatment planning may be based on predictions from an understanding of future states, as developed in step 305.

For example, step 305 may include determining, from the disease type and patient information, a prognosis for adverse cardiac events and plaque vulnerability. In one embodiment, step 305 may include predicting plaque growth using image characteristics analysis, geometrical analysis, computational fluid dynamics analysis, structural mechanics analysis, or any combination of these analyses of the anatomical image data. Alternatively or in addition, step 305 may employ a machine learning approach to compute plaque growth. Predicting plaque growth may include prognosis for adverse cardiac events and plaque vulnerability. An exemplary method for predicting plaque vulnerability is disclosed, for example, in U.S. Nonprovisional application Ser. No. 14/254,481, filed Apr. 16, 2014, entitled "Systems and Methods for Predicting Coronary Plaque Vulnerability from Patient-Specific Anatomic Image Data," which is hereby incorporated by reference herein in its entirety.

Figure 3C:
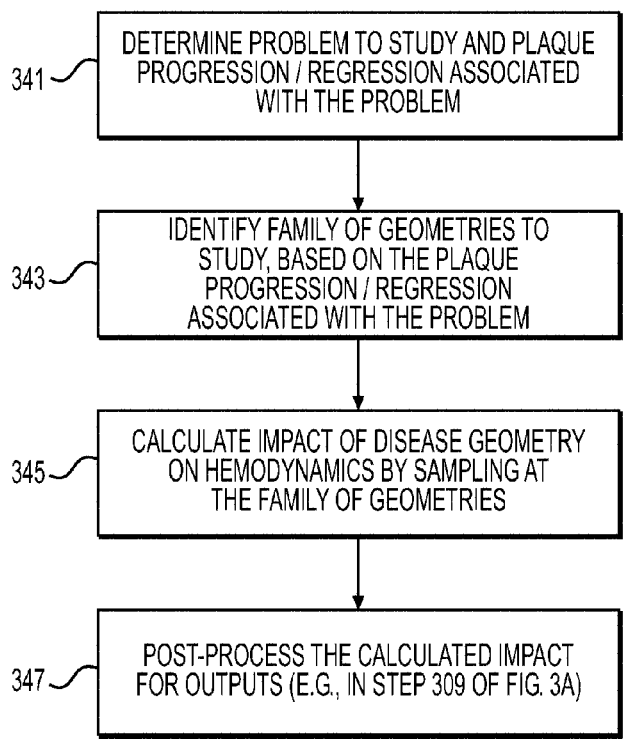
FIG. 3C is a block diagram of an exemplary method of analyzing the impact of disease progression and regression on hemodynamics, according to an exemplary embodiment of the present disclosure.

In one embodiment, step 307 may include an analysis of the functional significance of possible plaque growth/regression (e.g., from step 305). For example, step 307 may include determining hemodynamic response to the plaque growth/regression in order to assess functional significance of detected disease. Determining hemodynamic response may include evaluating the impact that plaque growth/regression may have on hemodynamics within respective portions of the blood vessels. FIG. 3C includes further detail regarding assessing the hemodynamic impact of disease progression and regression.

Step 309 may include determining an output. For example, step 309 may include quantifying and outputting disease risk. In some situations, step 309 may include post-processing output. The quantifying and post-processing of step 309 may include selecting an output (e.g., an output display) out of several possibly displays. Step 309 may further include creating renderings of displays or adjusting displays in response to user input or interaction. In one embodiment, step 309 may include writing all, or a combination of the following outputs to a disk and/or display device, or a generating the output as a report to a user (e.g., a physician). The outputs discussed below may be used individually, collectively, or in any combination.

In one embodiment, an output may include a combination of the type and growth of disease, along with hemodynamic sensitivity. Such an output may be used to assess disease risk and treatment options. For example, patients with predicted fast growth of disease and high hemodynamic sensitivity to disease geometry may be at a higher risk of heart disease. Patients with stable disease geometry may be at a lower risk. Patients with unstable disease geometry but low hemodynamic sensitivity may be labeled as having indeterminate risk. Patients with indeterminate risk may be candidates for frequent follow-ups or preventative medical therapy combined with close observations. An output may include a patient's risk level and one or more treatment recommendations based on the risk level.

In another embodiment, an output may include a characteristic curve for each identified disease region (e.g., from step 301 or method 320, step 329). For example, a hemodynamics characteristic curve may show how hemodynamic quantities of interest vary with disease geometry. For instance, each curve may correspond to a type of disease, where the curve may be plotted on a graph with geometry and a hemodynamic quantity of interest along the x-axis and y-axis.

In yet another embodiment, an output may include displaying one or more quantities of interest for a reconstructed geometry, as well as extrema of a family of geometries corresponding to disease progression and disease regression (e.g., as described in more detail in FIG. 3C). In some embodiments, the output may show quantities of interest for the extremes of disease progression/regression. In a further embodiment, an output may include a map of differences in hemodynamics, based on predictive modeling of progression or regression of disease at desired intervals, e.g., 3-month, 6-month, 1-year follow-up.

FIG. 3B is a block diagram of an exemplary method 320 of creating an anatomical model including diseased regions, according to an exemplary embodiment. The method of FIG. 3B may be performed by server systems 106, based on information, images, and data received from physicians 102 and/or third party providers 104 over electronic network 101.

Method 320 may be an optional process, performed when an anatomical model and/or information regarding location of disease and disease type is not already available.

In one embodiment, method 320 may begin with step 321 of acquiring, for instance, a digital representation encompassing an anatomy or system of interest. The digital representation may include an image-based representation, measured variables, a list or table of parameter values and features representative of the system, or a combination of the above. The digital representation may further be based on image scans, including CT, MRI, ultrasound, etc. saved using digital storage (e.g., a hard drive, network drive of a computer, laptop, server, or USB etc.). The representation acquired in step 321 may be of a specific individual's anatomy, and therefore be considered patient-specific.

In one embodiment, next steps may include isolating diseased segments. For example, step 323 may include isolating a system of interest within the anatomy shown in the digital representation. For example, when studying coronary artery disease, a system of interest may include the aorta and relevant coronary arteries. Step 323 may include pinpointing an area or region of an individual's vasculature as a system of interest. Alternately or in addition, step 323 may include defining characteristics of a system of interest, so that the system of interest may be identified within a set of information received regarding the individual's vasculature. For example, step 323 of may include delineating the geometry, specific conditions of the system of interest, and system properties. Specific conditions may include, for example, the diastolic phase at which an image was acquired. System properties may include date and time of image acquisition and a patient condition at the time of image acquisition, including blood pressure, height/weight, age, hematocrit/viscosity, etc. Patient conditions may vary over time, meaning, a single patient may undergo several patient conditions. For instance, a patient may be asymptomatic, then later experience symptoms of angina, then be post-acute myocardial infarction, emergency thrombolysis, and coronary stenting or CABG, or post-acute stroke and post-operation amputation. In another scenario, a patient may have newly diagnosed diabetes, cancer, stroke, dementia, and/or an aneurysm. In yet another situation, a patient may be bedridden, for example, due to trauma, stroke, dementia, etc. System properties may include the properties relating to and characterizing these various patient states. In some instances, step 323 may further include additional steps, for example, steps for image processing.

In one embodiment, method 320 may include step 325 of determining whether to reconstruct a system and/or portions of a system from a raw image (e.g., a raw image provided by step 321). Some embodiments may include generating reconstructions, for example, where the acquired representation (e.g., from step 321) may display an incomplete representation, or where the acquired representation includes variables or a list of parameter values, rather than an image-based model, or where image quality of the representation may be improved. From step 325, method 320 may either follow step 327 of creating a reconstruction, or step 329 of defining diseased regions in the patient representation.

In some embodiments, step 329 may follow step 327, in which case step 329 may include defining diseased regions in the reconstructed model (e.g., from step 327). In another embodiment, step 329 may include defining diseased regions from the representation received (e.g., from step 321) using the geometry, system properties, and/or specific conditions delineated in step 323. One exemplary case may include isolating and identifying stenoses where the system of interest includes lesions.

FIG. 3C is a block diagram of an exemplary method 340 of analyzing the impact of disease progression and regression on hemodynamics, according to an exemplary embodiment. The method of FIG. 3C may be performed by server systems 106, based on information, images, and data received from physicians 102 and/or third party providers 104 over electronic network 101. In one embodiment, method 340 may include analyzing an impact that disease progression and/or regression may have on hemodynamics, especially hemodynamics related to the system of interest. For example, method 340 may include computing hemodynamics corresponding to patient geometry (e.g., geometry available from step 301 or acquired and/or reconstructed from method 320 of FIG. 3B). In some cases, computing the hemodynamics may include solving Navier-Stokes equations to compute blood pressure and blood velocities, using boundary conditions specific to the anatomy and disease type. Exemplary methods for computing hemodynamics are disclosed, for example, in U.S. Nonprovisional application Ser. No. 14/447,195, filed Jul. 30, 2014, entitled "Method and System for Modeling Blood Flow with Boundary Conditions for Optimized Diagnostic Performance," which is hereby incorporated by reference herein in its entirety. Alternatively or in addition, computing the hemodynamics may include using a reduced order model or machine learning approach to compute hemodynamics.

In one embodiment, method 340 may include step 341 of identifying a problem to study, as well as the progression/regression of plaque to study associated with that problem. For example, for coronary artery lesions, the amount of progression or regression for coronary artery lesions may be in the range of a fraction of milliliters, depending on the size of a parent coronary artery. For another example, modeling soft plaques may involve modeling a larger change in progression and regression of lesions. In some embodiments, the amount of progression and regression of plaque may be in the form of percent change in a characteristic dimension. In other words, plaque characteristics (e.g., plaque vulnerability, composition, inflammatory status, etc.) may evolve in various disease conditions. By extension, progression and regression of plaque may be represented by a percent change in, for instance, plaque vulnerability, composition, inflammatory status, etc. as a disease progresses. Various diseases have respective effects on different areas in a vasculature. Thus, step 341 may include determining or identifying an amount of progression/regression to be studied that is appropriate for the disease and conditions of interest, for a particular individual.

In some embodiments, step 341 may include a threshold step of defining plaque progression and/or regression (e.g., prior to identifying progression/regression of plaque to study associated with a problem to study). Plaque composition may change over time. Also, progression and regression rates may vary over time, sometimes occurring simultaneously in different segments of one vessel, or in different vessels of a single patient. Furthermore, plaque may develop differently in various vascular beds (e.g., cerebrovascular, coronary, aorta, peripheral vasculature beds) simultaneously in throughout the patient's body. Identifying the progression/regression of plaque to study may include establishing a threshold definition for "plaque progression" versus "plaque regression."

Therefore, step 341 may include specifying a definition or set of conditions that comprise "plaque progression" and a definition or set of conditions that comprise "plaque regression." For example, one embodiment may include defining plaque progression as an increase in plaque volume. For such an embodiment, plaque regression may be defined as an enlargement of an artery in excess of plaque growth, resulting in a larger lumen. In other words, step 341 of defining plaque progression and/or regression may mean identifying "plaque regression" where lumen size increases, even if plaque also expands in volume. Similarly, a plaque rupture (e.g., erosion of the fibrous cap) may be classified as plaque progression by some definitions of plaque progression. However, plaque rupture may result in an enlarged lumen, less obstruction to blood flow, a higher $FFR_{CT}$. The situation involving an enlarged lumen, less obstruction to blood flow, and a higher $FFR_{CT}$ may be identified as "plaque regression." Finding the progression/regression of plaque to study may include more than an analysis of anatomic features (e.g., size, volume, lumen caliber, and flow (e.g., geometric anatomic-functional model). Therefore, step 341 may include a step of establishing definitions for "plaque progression" and "plaque regression" for the purposes of method 340.

In one embodiment, step 343 may include identifying or determining a family of geometries of interest. The progression/regression of the disease of interest may dictate the geometry to study. Then, step 343 may further include defining a family of interest, based on the amount of progression/regression to study. A family of geometries of interest may include a range of geometries and/or geometry characteristics. For example, a family of geometries may include a series of different geometries whose MLDs are near (e.g., +/−25%) the MLD of the reconstructed geometry, which may be sampled using the stochastic collocation method.

In one embodiment, step 345 may include sampling the family of geometries (e.g., as determined in step 343) to calculate the impact of disease geometry on hemodynamics. In one embodiment, step 345 may include sampling the family of geometries using a stochastic algorithm. In one embodiment, step 345 may further include a preliminary step of selecting and/or determining a sampling method. For example, a Monte-Carlo algorithm may be a default method to perform the sampling for step 345, where arbitrary geometries may be sampled from within the family of geometries uniformly. This process may depend on the number of disease regions (e.g., as identified by method 320 at FIG. 3B). Step 345 may then include selecting an alternative sampling method.

For example, an alternative sampling for step 345 may include using a stochastic collocation algorithm, where the geometries may be sampled based on quadrature points of the Smolyak algorithm. Further, these quadrature points may be adaptively sampled using the adaptive sparse grid collocation algorithm based on how sensitive hemodynamics are to specific diseases. An exemplary method for using an adaptive sparse grid algorithm is disclosed, for example, in U.S. Nonprovisional application Ser. No. 13/864,996, filed Apr. 17, 2013, entitled "Method and System for Sensitivity Analysis in Modeling Blood Flow Characteristics," which is hereby incorporated herein by reference in its entirety. In one embodiment, Navier-Stokes equations may be solved in each of the sampled geometries to evaluate hemodynamics in response to changes in geometry.

In one embodiment, step 347 may include post-processing solved fluid dynamics equations, for instance, to compute a plot of the impact of disease on hemodynamics. In one embodiment, step 347 may include outputting the relationship between hemodynamics and disease geometry (e.g., to step 309). In a further embodiment, step 347 may include storing the information. The information may then be retrieved for step 309, wherein the information calculated in step 347 may be plotted and organized or processed into renderings and/or reports.

An alternative to method 340 may include a machine learning approach, where the approach may iteratively calculate the impact of disease geometry on hemodynamics. Exemplary methods for machine learning approaches are disclosed, for example, in U.S. Nonprovisional application Ser. No. 14/011,151, filed Aug. 27, 2013, entitled "Systems and Methods for Predicting Location, Onset, and/or Change of Coronary Lesions," in U.S. Nonprovisional application Ser. No. 13/895,893 filed May 16, 2013, U.S. Nonprovisional application Ser. No. 13/895,871 filed May 16, 2013, and in U.S. Nonprovisional application Ser. No. 13/864,996, filed Apr. 17, 2013, entitled "Method and System for Sensitivity Analysis in Modeling Blood Flow Characteristics," which are hereby incorporated by reference herein in its entirety.

Figure 4A:
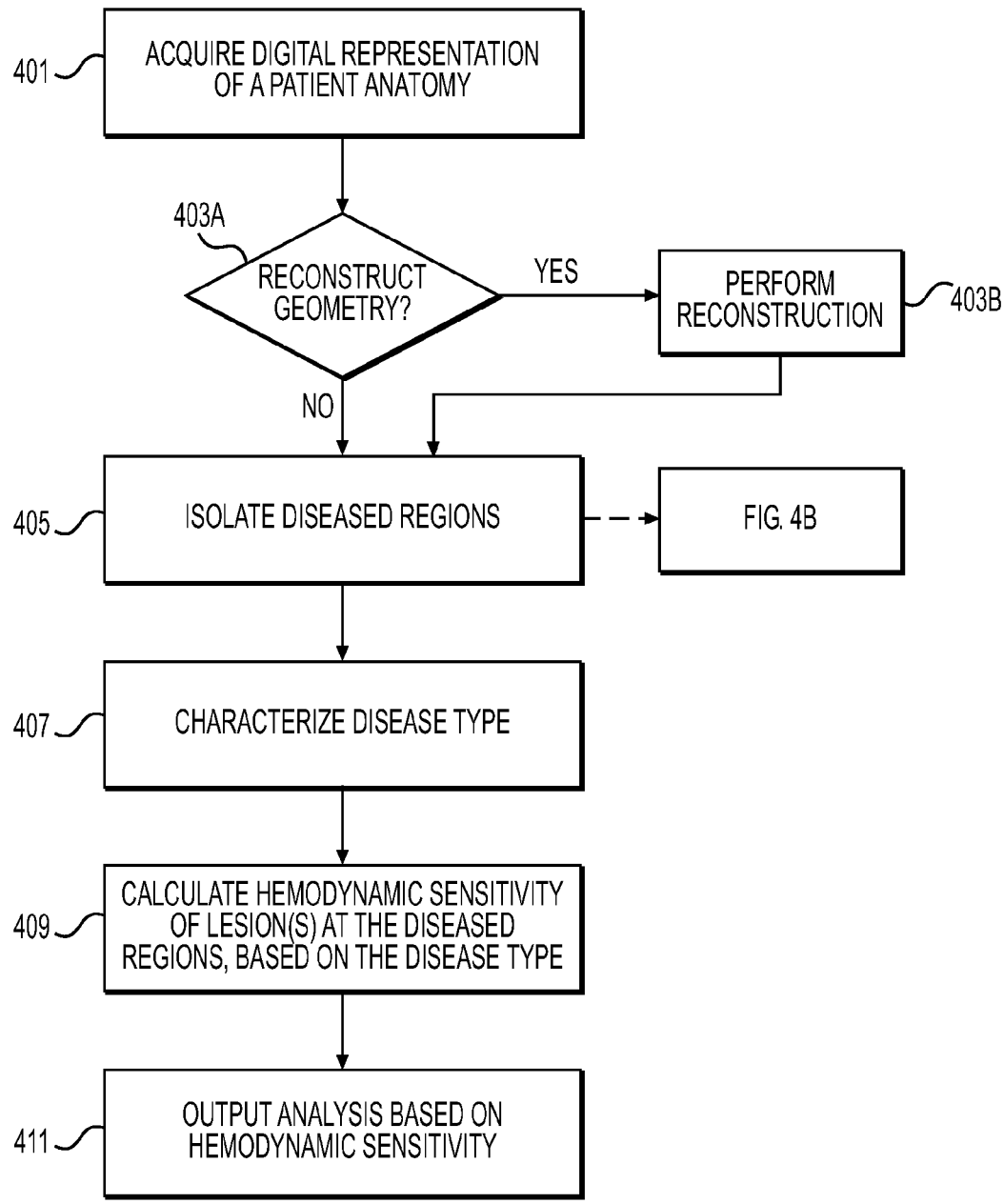
FIG. 4A is a block diagram of an exemplary method of a specific embodiment for treatment planning based on plaque progression/regression curves for coronary artery disease, according to an exemplary embodiment of the present disclosure.

FIG. 4A is a block diagram of an exemplary method 400 of a specific embodiment for treatment planning based on plaque progression/regression curves for artery disease (e.g., coronary artery disease), according to an exemplary embodiment. The method of FIG. 4A may be performed by server systems 106, based on information, images, and data received from physicians 102 and/or third party providers 104 over electronic network 101. In one embodiment, step 401 may include acquiring a digital representation of a system, for instance, a patient anatomy. In one embodiment, the digital representation (e.g., the memory or digital storage (e.g., hard drive, network drive) of a computational device such as a computer, laptop, DSP, server, etc.) may include an image scan of an individual, including the ascending aorta and coronary artery tree. The image scan may include scans from cardiac computed tomography (CCTA), MRI, ultrasound, etc. The digital representation may further include a set of clinical parameters, including heart-rate, systolic and diastolic brachial blood pressures, hematocrit, patient height and weight, patient history such as smoking status, presence/absence of diabetes, medicines used (e.g., antihypertensives, statins, etc.), etc.

In one embodiment, steps 403A and 403B may include preparing digital representations of the regions of interest. In some embodiments, steps 403A and 403B may include determining that the received representation (e.g., from step 401) includes regions of interest. In another embodiment, step 403A and 403B may include reconstructing portions of the patient's anatomy before isolating one or more regions of interest. For example, step 403A may include a determination as to whether to reconstruct at least a portion of the patient anatomy. If reconstruction(s) are desired, step 403B may follow step 403A, in which step 403B may include performing the desired reconstruction. For example, step 403B may include computing centerlines, which pass through the centers of respective vessels of interest. Lumen segments may be constructed manually or automatically to identify voxels belonging to the aorta and to the lumen of the coronary arteries. Once all relevant voxels are identified, step 403B may further include generating a geometric model of the aorta and relevant coronary arteries may be reconstructed.

Figure 4B:
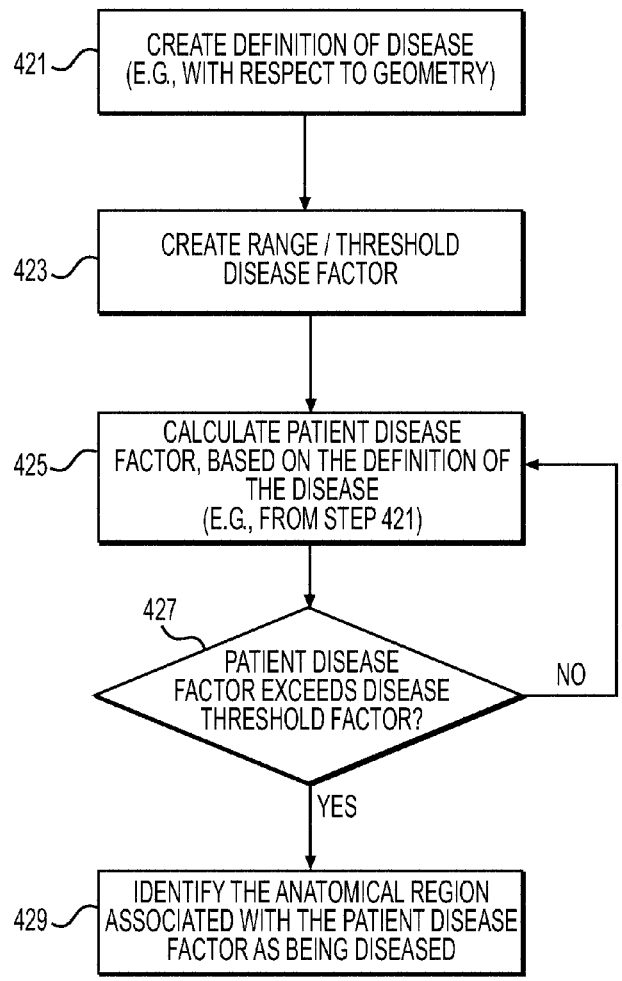
FIG. 4B is a block diagram of an exemplary method for finding a diseased region of anatomy, according to an exemplary embodiment of the present disclosure.

In one embodiment, step 405 may follow either of steps 403A and 403B. Step 405 may include isolating diseased locations of the regions of interest. FIG. 4B includes a more detailed breakdown of exemplary steps for isolating diseased locations. In one embodiment, step 405 may employ a basic threshold for merely detecting whether a location is diseased or not diseased. Subsequent steps involve understanding the disease detected and its impact on an individual's health.

In one embodiment, step 407 may include characterizing the disease type. In other words, step 407 may involve profiling a disease at each of the diseased sites. For example, step 405 may yield a binary indication of whether or not a region is diseased. Step 407 may involve describing identified disease at respective portions of the representation. In one embodiment, characterizing disease type may include determining or recognizing various classifications of disease. For example, type of disease may be broadly classified as lesions with a lipid rich core (soft plaque), collagen fibers (fibrotic), or hardened calcified plaque. Soft plaques may be first classified based on constitutive components, e.g., fraction of lipid, necrotic core, macrophages, collagen fibers, etc. Step 407 may include categorizing the diseased locations isolated and identified in step 405, based on the determined and/or recognized classifications of disease. For example, classifications may be based on or similar to method 200 of FIG. 2.

Alternately or in addition, characterizing disease type in step 407 may include classifying the disease at the diseased regions, e.g., by propensity of plaque to remodel. In one embodiment, such classification may include using a remodeling index. Step 407 may further include calculating such a remodeling index. For example, a remodeling index may be estimated from the relationship between plaque progression and one or more of: patient risk factors, medicines used by a patient, hemodynamic forces, and structural composition of the plaque. The remodeling index may be estimated using a machine learning approach by using follow-up patient data, and mapping features of disease (e.g., composition, location, hemodynamic forces, etc.) to lesion remodeling.

Alternatively, the remodeling index may be estimated using a modeling approach. For instance, a modeling approach may include computing a remodeling index by solving Navier-Stokes equations with appropriate boundary conditions to calculate the forces acting on plaque. These forces may be used along with structural properties of the plaque to find homeostatic plaque configuration, for example, by solving stress equilibrium equations.

Step 409 may include calculating hemodynamic sensitivity of a lesion. One embodiment of step 409 may thus include calculating limits of plaque geometry. For example, the plaque remodeling index computed in step 407 may be used to calculate the limits of plaque geometry. In some cases, the limits of plaque geometry may include the maximum size that a plaque may reach in a region, due to factors, e.g., before completely occluding a vessel, breaking off, destabilizing, etc. For instance, the plaque remodeling index may quantify the limits of plaque geometry as a relationship between a (reference) vessel cross-sectional area and a point of maximum stenosis. Maximal vessel stenosis may be measured from the luminal-intimal boundary to the outer vessel wall. A plaque characteristic curve may be estimated assuming a uniform variability of the plaque geometry within the limits of plaque geometry.

In one embodiment, analyzing hemodynamic sensitivity of a lesion may include a stochastic collocation method. For example, step 409 may include initializing stochastic collocation (quadrature) points using the Smolyak sparse grid algorithm, with each of the stochastic collocation points corresponding to a unique plaque geometry. In some cases, the number of collocation points may depend on the collocation (quadrature) level. In addition, collocation levels may be nested, e.g., with level 0 corresponding to one simulation and the number increasing with levels. The actual number of collocation points may depend on how sensitive the hemodynamic solutions are to the disease geometry.

Then, for each identified geometry with a corresponding stochastic collocation point, step 409 may include estimating $FFR_{CT}$. For example, $FFR_{CT}$ may be estimated either by solving Navier-Stokes equations using CFD methods, or by using a machine learning surrogate based on patient-specific features. An exemplary method for estimating FFR is disclosed, for example, in U.S. Nonprovisional application Ser. No. 13/864,996, filed Apr. 17, 2013, entitled "Method and System for Sensitivity Analysis in Modeling Blood Flow Characteristics," which is hereby incorporated by reference herein in its entirety. Step 409 may involve identifying the hemodynamic sensitivity of a lesion by calculating $FFR_{CT}$.

In one embodiment, step 411 may include outputting analyses based on the plaque information in connection to hemodynamic sensitivity information. For example, step 411 may include outputting a patient risk map and/or treatment options. In a further example, step 411 may include a selection of several displays for patient risk maps and/or treatment options. Risk and treatment may be displayed in a variety of ways. In one instance, a display may include a plot showing the hemodynamic sensitivity for each lesion identified. Disease type (e.g., from step 407) may be included as annotations for each of the lesions, e.g., in a display created for a display device. The display may further be included as a report, e.g., for a physician. In one embodiment, the display and/or report may also include a treatment option (e.g., a treatment option selected from a chart described in FIG. 2). For example, for an individual with slightly positive $FFR_{CT}$ (e.g., 0.78) and plaques that are highly sensitive to plaque regression, lipid lowering agents (e.g., statin treatments) may be coupled to a treatment option, such as lifestyle modifications. Lifestyle modification may include, for example, smoking cessation, control of dietary habits, frequent exercise (e.g., running), or managing stress levels. For an individual having a negative $FFR_{CT}$ (e.g., 0.85) and soft plaque that is highly sensitive to progression, frequent follow-up monitoring may be considered. For $FFR_{CT}$ positive patients with plaques sensitive to progression, surgical alternatives such as stenting may be optimal. In some embodiments, treatment planning (e.g., following method 200 in FIG. 2) may be mapped to a risk score.

Figure 5:
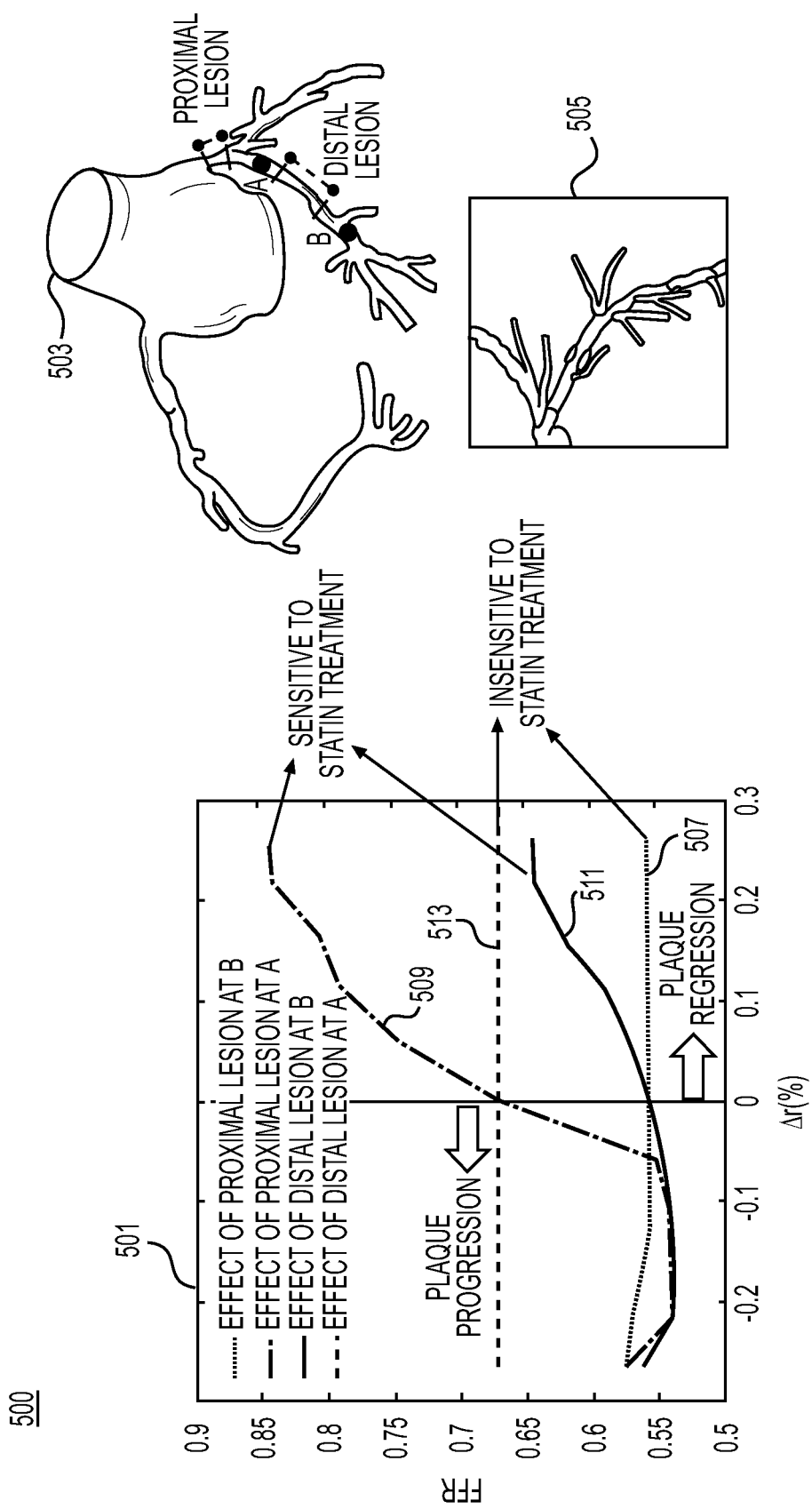
FIG. 5 shows an exemplary display including plaque progression/regression curves for a soft lipid-rich plaque, according to an embodiment of the present disclosure.

In another example, a display may include $FFR_{CT}$ maps corresponding to the extrema of plaque progression or regression (e.g., identified in step 409 and corresponding to the extrema of stochastic collocation points). Such maps may represent the worst state and best state of hemodynamics within the range identified using a plaque remodeling index. In yet another example, a display may include a sensitivity map for each lesion (e.g., as identified in step 409), where the sensitivity in the map may correspond to the relationship between $FFR_{CT}$ and positive and/or negative remodeling of the respective lesion. Typically, $FFR_{CT}$ sensitivity may be highest in regions downstream of a plaque, but sensitivity may also be affected by regions proximal to a plaque if respective lesions are flow-limiting. This type of map may help identify the relative impact of serial lesions, or help decide if stenting is hemodynamically beneficial. FIGS. 5-7 include exemplary displays, e.g., $FFR_{CT}$ maps, shown through visual representations on a diagram or model.

FIG. 4B is a block diagram of an exemplary method 420 for finding a diseased region, according to an exemplary embodiment. The method of FIG. 4B may be performed by server systems 106, based on information, images, and data received from physicians 102 and/or third party providers 104 over electronic network 101. In one embodiment, step 421 may include creating or receiving a definition of disease. Disease may be defined with respect to geometry. For example, disease may be defined based on lumen narrowing in coronary arteries. This may include defining disease as a ratio of lumen radius to healthy lumen radius. Healthy lumen radius may be calculated, in some cases, using maximum lumen radius in a coronary segment, average lumen radius in the coronary segment, or by fitting a global radius curve for a coronary artery based on patient-specific lumen radius (e.g., using Gaussian kernel regression). Step 421 may include defining a disease factor, for example, $$d=1-r/r_{healthy}, \text{ if } r<r_{healthy}, \text{ and}$$

$$d=0, \text{ if } r<r_{healthy}.$$

In one embodiment, step 423 may include determining a threshold disease factor, or disease factor range. The threshold disease factor or disease factor range may dictate whether a region of geometry is considered diseased, for the purposes of method 400. In one embodiment, step 425 may include applying patient-specific data to the definition (e.g., as specified in step 421). In some instances, step 425 may include retrieving geometry (e.g., "r" from the disease factor definition) from the geometric model of step 401. Then, the disease definition may be applied to the retrieved geometry. In other words, step 425 may include computing a patient-specific disease factor. Step 427 may include comparing the computed patient disease factor, to the threshold disease factor or disease factor range (e.g., from step 423). From the comparison, step 429 may include determining whether disease exists at a geometric region at the location of input patient information. For example, $d_{threshold}$ may be a value of 0.25, and coronary artery disease may exist at locations where $d>d_{threshold}$. This means step 429 may designate regions of a patient geometry where a disease factor is computed to exceed 0.25, as diseased regions.

Figure 4C:
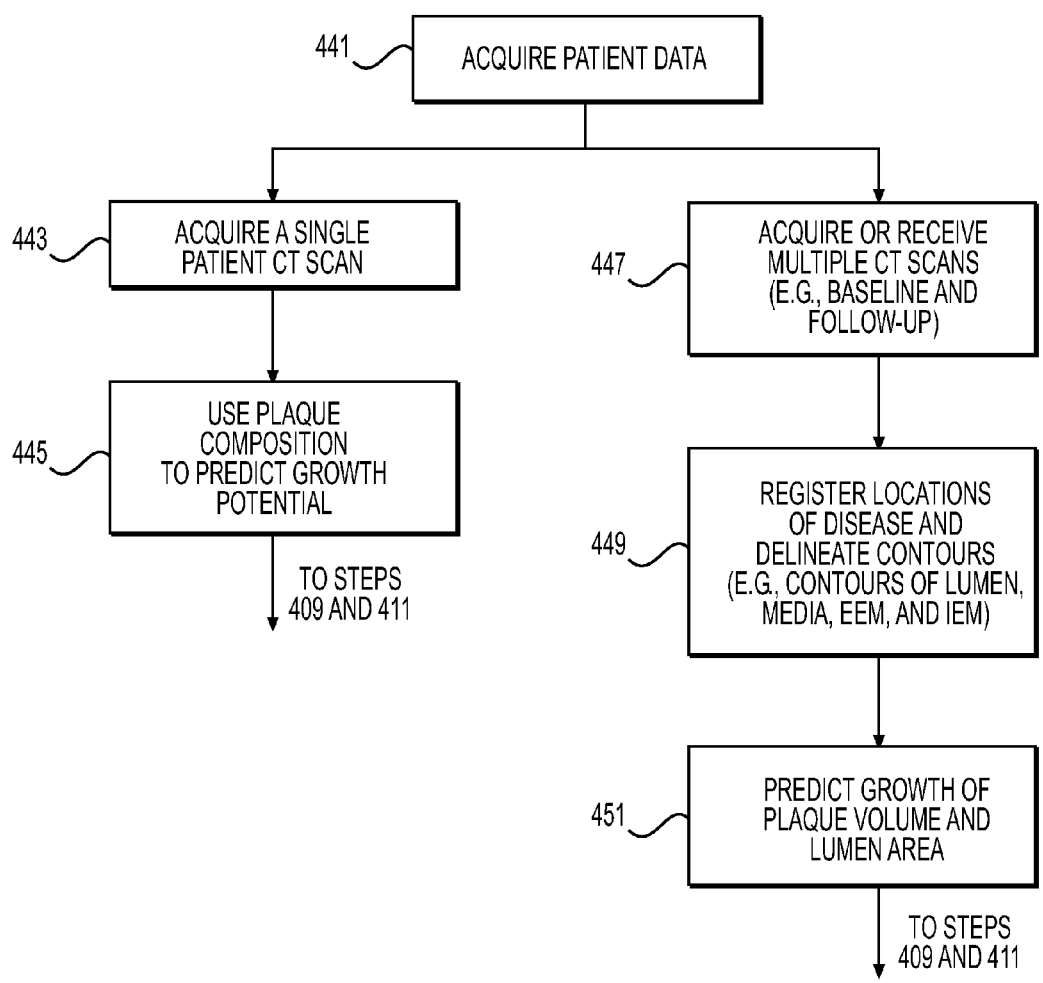
FIG. 4C is a block diagram of an exemplary method for characterizing a disease type, according to an exemplary embodiment of the present disclosure.

FIG. 4C is a block diagram of an exemplary method 440 for characterizing a disease type, according to an exemplary embodiment. The method of FIG. 4C may be performed by server systems 106, based on information, images, and data received from physicians 102 and/or third party providers 104 over electronic network 101. Method 440 may include characterizing a disease type in terms of the ability of plaque to remodel (e.g., plaque volume growth potential and resulting lumen area coinciding with plaque growth).

In one embodiment, step 441 includes acquiring data, for instance, patient data. Patient data may include patient information including, for example, age, demographic, anatomy (e.g., digital representations), medical history, etc. Step 443 may include acquiring a single scan (e.g., a CT scan) of patient anatomy. This step may be similar to step 401 of acquiring a digital representation of a patient anatomy. Step 445 may include using plaque composition to predict growth potential of the plaque volume. In one embodiment, such a prediction may involve the steps of method 200, including analyses of calcified plaque versus soft plaque, as well as growth potential associated with the calcified versus soft plaque. Following this step, method 440 may proceed with calculating hemodynamic sensitivity at diseased regions based on a disease type (e.g., a disease type based on the predicted growth potential derived from plaque composition analysis) and outputting an analysis based on hemodynamic sensitivity (steps 409 and 411, respectively).

Alternately or in addition, method 440 may include step 447 of acquiring and/or receiving multiple CT scans, if the scans are available. For example, the multiple CT scans may be associated with a patient at various states and/or times (e.g., patient baseline scan and follow-up scans). Alternately or in addition, the multiple CT scans may include scans of individuals other than the patient, e.g., scans of the other individuals at various states and/or times. In one embodiment, step 449 may include registering locations of disease and delineating contours of patient (or individual) anatomy (e.g., contours of lumen, media, external elastic membrane (EEM), and internal elastic membrane (IEM)). In one embodiment, step 451 may include predicting growth of plaque volume based on the locations of disease and contours of anatomy. Alternately or in addition, step 451 may include predicting lumen area using the locations of disease and contours of anatomy from step 449. Upon determining plaque remodeling characteristics from steps 447, 449, and 451, method 440 may proceed with steps 409 and 441 (e.g., calculating hemodynamic sensitivity at diseased regions based on a disease type and outputting an analysis based on hemodynamic sensitivity, respectively).

FIG. 5 shows an exemplary electronic display 500 including plaque progression/regression curves for a soft lipid-rich plaque, in accordance with an embodiment of the present disclosure. Electronic display 500 may be generated on any type of electronic device, such as a computer screen, mobile screen, projection, etc., and on any display type, such as a software interface, website, etc. In one embodiment, one output may include a plot 501 of plaque progression/regression curves for a soft lipid rich plaque, a location diagram 503, and a 3-D patient-specific model 505. For example, plot 501 may chart FFR against a change in lesion radius (e.g., where change in lesion radius may be expressed as a percentage change). In one case, the plot 501 may focus on how FFR evolves in response to various radii (or MLD) of plaque, for instance in a range, where $\Delta r=-25\%$ to $25\%$. In one embodiment, diagram 503 may depict lesion(s) and locations near the lesion(s) (e.g., location A and location B).

In one embodiment, plot 501 may include progression/regression curve 507 for the effect of a proximal lesion experienced at location B, curve 509 for the effect of the proximal lesion experienced at location A, curve 511 for the effect of a distal lesion experienced at location B, and curve 513 for the effect, at location A, experienced as a result of the distal lesion. Plot 501 may indicate that the severity of a lesion, the impact of a lesion on blood flow, as well as a region where sensitivity is calculated as being relatively high, may be important in detecting treatments related to plaque progression/regression. For example, curve 507 may show that location B experiences little change in FFR in response to change in radius at the proximal lesion. Similarly, curve 513 may indicate that, at location A, FFR experiences little change in FFR coming from the distal lesion. Curves 509 and 511, however, may show far more hemodynamic sensitivity in response to plaque progression and regression at location A from the proximal lesion and at location B from the distal lesion, respectively.

Thus, curve 507 may show location B to be insensitive to statin treatment with respect to the proximal lesion and curve 513 may show location A to be insensitive to statin treatment with respect to the distal region. Meanwhile, curve 509 may indicate that location A may be sensitive to statin treatment with respect to the proximal lesion and curve 511 may show location B to be sensitive to statin treatment at the distal lesion. From the progression/regression curves, a user may determine, for instance, a target FFR level to reach, and determine or select a treatment that may help a patient achieve the target FFR.

In one embodiment, model 505 may include an option to scroll to better pinpoint or view the locations in a 3-D view. Model 505 and diagram 503 may further include options to select other locations, like locations A and location B, and/or locations for lesions. Further, model 505 and diagram 503 may show simulations of treatment application, for instance, a color-coded simulation illustrating blood flow at various locations, after statin treatment.

FIG. 6 shows an exemplary electronic display 600 including plaque progression/regression curves for a soft lipid-rich plaque, in accordance with an embodiment of the present disclosure. Electronic display 600 may be generated on any type of electronic device, such as a computer screen, mobile screen, projection, etc., and on any display type, such as a software interface, website, etc. In one embodiment, an output may, again, include a plot 601, diagram 603, and 3-D model 605. The plot 601 may include a plaque regression/progression curve for multiple lesions. In the embodiment shown in plot 601, the regression/progression curves may be associated with serial lesions. For example, the serial lesions may be three serial lesions in the left anterior descending (LAD) artery for a calcified plaque (e.g., shown at diagram 603 as a distal lesion 607, middle lesion 609, and proximal lesion 611). In other words, plot 601 may show the impact of three plaques on FFR at various measurement locations. Model 605 may further show the LAD, e.g., in a 3-D view.

In one embodiment, diagram 603 and/or model 605 may include visual representations of hemodynamic sensitivity and/or simulated blood flow, e.g., with color-coding or annotations. In one embodiment, diagram 603 and/or model 605 may include options to change views (e.g., zoom in/zoom out functions, scrolling, rotation, etc.). Model 605 and diagram 603 may further include options to select other locations to observe.

FIG. 7 shows an exemplary electronic display 700 of $FFR_{CT}$ variation due to remodeling of a lesion, in accordance with an embodiment of the present disclosure. Electronic display 700 may be generated on any type of electronic device, such as a computer screen, mobile screen, projection, etc., and on any display type, such as a software interface, website, etc. In one embodiment, display 700 may include a model 701, along with various plots of FFR variation. Display 700 may be an alternative way to show the relationship between FFR and plaque type and geometry. In one embodiment, model 701 may show a lesion, e.g., through color variation and/or annotations. Then, exemplary plots 703-711 may show $FFR_{CT}$ variation at various places near and along the lesion, from an upstream location to downstream locations. In one embodiment, model 701 may depict change in $FFR_{CT}$ by color (or another visual representation), and plots 703-711 may contain more detail on the trend in $FFR_{CT}$ variation at each location. In one embodiment, a user may interact with model 701. For example, a user may scroll along the lesion shown, where plots may adjust according to the location of the scrolling. As with diagrams and models from display 500 and display 600, display 700 may permit user selection and various functions or options in views of the model 701. In the example shown for FIG. 7, $FFR_{CT}$ downstream of a lesion may increase due to reduced pressure drop when plaque positively remodels. Also, $FFR_{CT}$ upstream may experience a slight drop due to increased flow rate immediately upstream of a lesion.

This disclosure may additionally apply to computing hemodynamic quantities of interest, beyond FFR in the coronary arteries. For example, in additional or alternate embodiments, the sensitivity of blood flow rate, tissue perfusion, pressure, shear stress, plaque force, or rupture risk on plaque progression or regression may be assessed.

Alternate embodiments of the invention may apply to quantifying the effect of progression or regression of atherosclerotic plaques in the carotid artery, intracranial cerebral arteries, superficial femoral artery and renal artery, etc. In each of the cases, this invention may be used to quantify the effect of plaque geometry changes on relevant hemodynamic quantities, including blood flow rate, blood pressure, or tissue perfusion.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of evaluating a patient with vascular disease, the method comprising:
   receiving patient-specific data regarding a geometry of the patient's vasculature;
   determining a plaque remodeling characteristic characterizing a propensity of the disease in the patient's vasculature to progress or regress;
   determining, using the received patient-specific data and the determined plaque remodeling characteristic, a geometric model of a progression or regression of disease at a location in the patient's vasculature;
   calculating a value of a blood flow characteristic within the patient's vasculature using a blood flow model determined based on the received patient-specific data and the determined plaque remodeling characteristic; and
   generating a treatment recommendation or risk assessment based on the value of the blood flow characteristic calculated using the blood flow model based on the received patient-specific data and the determined plaque remodeling characteristic.

2. The computer-implemented method of claim 1, wherein the treatment recommendation includes medication, stenting, bypass grafting, dietary changes, an exercise regimen, or a combination thereof.

3. The computer-implemented method of claim 1, further comprising:
   determining a disease type associated with the location of disease or composition of the disease, wherein the treatment recommendation is further associated with the determined disease type.

4. The computer-implemented method of claim 3, wherein the disease type includes plaque type, including soft plaque, calcified plaque, or fibrotic plaque.

5. The computer-implemented method of claim 1, further comprising identifying the location as a candidate location for treatment, based on the calculated value of the blood flow characteristic.

6. The computer-implemented method of claim 1, wherein the blood flow characteristic includes a value of fractional flow reserve.

7. The computer-implemented method of claim 1, wherein the modeled progression or regression of disease at the location in the patient's vasculature includes accounting for a change in geometry of the patient's vasculature.

8. The computer-implemented method of claim 1, wherein the disease includes the presence of plaque.

9. A system for evaluating a patient with vascular disease, the system comprising:
   a data storage device storing instructions for evaluating a patient with vascular disease; and
   a processor configured to execute the instructions to perform a method including:
      receiving patient-specific data regarding a geometry of the patient's vasculature;
      determining a plaque remodeling characteristic characterizing a propensity of the disease in the patient's vasculature to progress or regress;
      determining, using the received patient-specific data and the determined plaque remodeling characteristic, a geometric model of a progression or regression of disease at a location in the patient's vasculature;
      calculating a value of a blood flow characteristic within the patient's vasculature using a blood flow model determined based on the received patient-specific data and the determined plaque remodeling characteristic; and
      generating a treatment recommendation or risk assessment based on the value of the blood flow characteristic calculated using the blood flow model based on the received patient-specific data and the determined plaque remodeling characteristic.

10. The system of claim 9, wherein the treatment recommendation includes medication, stenting, bypass grafting, dietary changes, an exercise regimen, or a combination thereof.

11. The system of claim 9, wherein the system is further configured for:
   determining a disease type associated with the location of disease or composition of the disease, wherein the treatment recommendation is further associated with the determined disease type.

12. The system of claim 11, wherein the disease type includes plaque type, including soft plaque, calcified plaque, or fibrotic plaque.

13. The system of claim 9, further comprising identifying the location as a candidate location for treatment, based on the calculated value of the blood flow characteristic.

14. The system of claim 9, wherein the blood flow characteristic includes a value of fractional flow reserve.

15. The system of claim 9, wherein the modeled progression or regression of disease at the location in the patient's vasculature includes accounting for a change in geometry of the patient's vasculature.

16. The system of claim 9, wherein the disease includes the presence of plaque.

17. A non-transitory computer readable medium for use on a computer system containing computer-executable programming instructions for performing a method of evaluating a patient with vascular disease, the method comprising:
   receiving patient-specific data regarding a geometry of the patient's vasculature;
   determining a plaque remodeling characteristic characterizing a propensity of the disease in the patient's vasculature to progress or regress;
   determining, using the received patient-specific data and the determined plaque remodeling characteristic, a geometric model of a progression or regression of disease at a location in the patient's vasculature;
   calculating a value of a blood flow characteristic within the patient's vasculature using a blood flow model determined based on the received patient-specific data and the determined plaque remodeling characteristic; and
   generating a treatment recommendation or risk assessment based on the value of the blood flow characteristic calculated using the blood flow model based on the received patient-specific data and the determined plaque remodeling characteristic.

18. The non-transitory computer readable medium of claim 17, wherein the treatment recommendation includes medication, stenting, bypass grafting, dietary changes, an exercise regimen, or a combination thereof.

19. The non-transitory computer readable medium of claim 17, the method further comprising:

determining a disease type associated with the location of disease or composition of the disease, wherein the treatment recommendation is further associated with the determined disease type.

20. The non-transitory computer readable medium of claim 19, wherein the disease type includes plaque type, including soft plaque, calcified plaque, or fibrotic plaque.

* * * * *